US010324045B2

(12) United States Patent
Cui et al.

(10) Patent No.: US 10,324,045 B2
(45) Date of Patent: Jun. 18, 2019

(54) SURFACE DEFECT INSPECTION WITH LARGE PARTICLE MONITORING AND LASER POWER CONTROL

(71) Applicant: KLA-Tencor Corporation, Milpitas, CA (US)

(72) Inventors: Steve (Yifeng) Cui, Fremont, CA (US); Chunsheng Huang, Milpitas, CA (US); Chunhai Wang, Pleasanton, CA (US); Christian Wolters, San Jose, CA (US); Bret Whiteside, San Jose, CA (US); Anatoly G. Romanovsky, Palo Alto, CA (US); Chuanyong Huang, San Jose, CA (US); Donald Warren Pettibone, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 121 days.

(21) Appl. No.: 15/230,330

(22) Filed: Aug. 5, 2016

(65) Prior Publication Data
US 2018/0038803 A1 Feb. 8, 2018

(51) Int. Cl.
*G01N 21/88* (2006.01)
*G01N 21/00* (2006.01)
(Continued)

(52) U.S. Cl.
CPC ..... *G01N 21/9501* (2013.01); *G01N 21/8806* (2013.01); *G01N 21/956* (2013.01)

(58) Field of Classification Search
CPC ............... G01N 21/8806; G01N 21/94; G01N 21/9501; G01N 2021/8835; G01N 2201/06113
(Continued)

(56) References Cited

U.S. PATENT DOCUMENTS 5,864,394 A 1/1999 Jordan et al.
6,201,601 B1 3/2001 Vaez-Iravani et al.
(Continued)

FOREIGN PATENT DOCUMENTS

JP 2000-260376 A 9/2000
JP 2003-017536 A 1/2003
(Continued)

OTHER PUBLICATIONS

International Search Report dated Nov. 15, 2017, for PCT Application No. PCT/US2017/045261 filed on Aug. 3, 2017 by KLA-Tencor Corporation, 3 pages.

*Primary Examiner* — Sunghee Y Gray
(74) *Attorney, Agent, or Firm* — Spano Law Group; Joseph S. Spano

(57) ABSTRACT

Methods and systems for reducing illumination intensity while scanning over large particles are presented herein. A surface inspection system determines the presence of a large particle in the inspection path of a primary measurement spot using a separate leading measurement spot. The inspection system reduces the incident illumination power while the large particle is within the primary measurement spot. The primary measurement spot and the leading measurement spot are separately imaged by a common imaging collection objective onto one or more detectors. The imaging based collection design spatially separates the image of the leading measurement spot from the image of the primary measurement spot at one or more wafer image planes. Light detected from the leading measurement spot is analyzed to determine a reduced power time interval when the optical power of the primary illumination beam and the leading illumination beam are reduced.

20 Claims, 9 Drawing Sheets

(51) Int. Cl.
*G01N 21/95* (2006.01)
*G01N 21/956* (2006.01)

(58) Field of Classification Search
USPC ...................................................... 356/237.5
See application file for complete search history.

(56) References Cited

U.S. PATENT DOCUMENTS

| | | |
|---|---|---|
| 6,204,918 B1 | 3/2001 | Isozaki et al. |
| 6,208,411 B1 | 3/2001 | Vaez-Iravani et al. |
| 6,271,916 B1 | 8/2001 | Marxer et al. |
| 6,341,042 B1 | 1/2002 | Matsunaka et al. |
| 6,466,315 B1 | 10/2002 | Karpol et al. |
| 6,529,270 B1 | 3/2003 | Bills |
| 6,608,676 B1 | 8/2003 | Zhao et al. |
| 7,130,039 B2 | 10/2006 | Vaez-Iravani et al. |
| 7,295,303 B1 | 11/2007 | Vaez-Iravani et al. |
| 7,426,023 B2 | 9/2008 | Ohshima et al. |
| 7,436,508 B2 | 10/2008 | Wolters et al. |
| 7,492,451 B2 | 2/2009 | Vaez-Iravani et al. |
| 7,671,982 B2 | 3/2010 | Wolters et al. |
| 7,787,114 B2 | 8/2010 | Wolters et al. |
| 7,952,083 B2 | 5/2011 | Shichi et al. |
| 8,194,240 B1 | 6/2012 | Vaez-Iravani et al. |
| 8,755,044 B2 | 6/2014 | Reich et al. |
| 8,885,158 B2 | 11/2014 | Wolters et al. |
| 9,116,132 B2 | 8/2015 | Wolters et al. |
| 9,255,891 B2 | 2/2016 | Wolters et al. |
| 2003/0103203 A1 | 6/2003 | Isozuki et al. |
| 2004/0076322 A1 | 4/2004 | Avishay |
| 2004/0263835 A1 | 12/2004 | Miyakawa et al. |
| 2005/0170569 A1 | 8/2005 | Yazaki et al. |
| 2006/0103856 A1 | 5/2006 | Miyakawa et al. |
| 2006/0256325 A1 | 11/2006 | Mcmillan et al. |
| 2008/0159112 A1 | 7/2008 | Van Der Lee et al. |
| 2009/0224180 A1 | 9/2009 | Aigner |
| 2009/0225399 A1 | 9/2009 | Zhao et al. |
| 2009/0299655 A1 | 12/2009 | Biellak et al. |
| 2010/0093112 A1 | 4/2010 | Takagi et al. |
| 2010/0195097 A1 | 8/2010 | Wenz |
| 2010/0274392 A1 | 10/2010 | Igari et al. |
| 2012/0314211 A1 | 12/2012 | Ando et al. |
| 2013/0016346 A1 | 1/2013 | Romanovsky et al. |
| 2013/0050689 A1 | 2/2013 | Reich et al. |
| 2015/0369753 A1* | 12/2015 | Romanovsky ..... G01N 21/9501 356/237.5 |
| 2016/0334652 A1* | 11/2016 | Sakuma ................ H01S 3/2391 |
| 2018/0017502 A1* | 1/2018 | Makuuchi .......... G01N 21/8806 |

FOREIGN PATENT DOCUMENTS

| | | |
|---|---|---|
| JP | 2007-279026 A | 10/2007 |
| JP | 20100236966 A | 10/2010 |
| JP | 2011-009554 A | 1/2011 |

* cited by examiner

SURFACE DEFECT INSPECTION WITH LARGE PARTICLE MONITORING AND LASER POWER CONTROL

TECHNICAL FIELD

The described embodiments relate to systems for surface inspection, and more particularly to semiconductor wafer inspection modalities.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

One such inspection system is a surface inspection system that illuminates and inspects an unpatterned wafer surface for undesired particles. As semiconductor design rules continue to evolve, the minimum particle size that must be detected by a surface inspection system continues to shrink in size.

To detect smaller particles, laser scattering based inspection tools must increase the laser power density of the illumination light. However, in some examples, high illumination power density causes large size particles to explode due to high power laser heating. This creates hundreds of smaller particles on the wafer and compounds the contamination problem. In other examples, higher illumination power density damages films deposited on the wafer or the wafer itself.

Typically, overall incident beam power is reduced by dumping a portion of the illumination light generated by the illumination source to avoid reaching the thermal damage threshold. In some examples, a significant amount of the beam power generated by the illumination source is dumped to avoid damaging the wafer. In typical bare wafer applications that are shot noise limited, the loss of overall beam power results in a loss of defect detection sensitivity.

Improvements to scanning surface inspection systems are desired to detect defects in the inspection path of an illumination spot on a wafer surface with greater sensitivity while avoiding large particle fragmentation and thermal damage to the wafer surface.

SUMMARY

Methods and systems for reducing illumination intensity when scanning over large particles are presented herein. A surface inspection system determines the presence of a large particle in the inspection path of a primary measurement spot using a separate leading measurement spot. The inspection system reduces the incident illumination power before high power illumination reaches the large particle.

In one aspect, both the primary measurement spot and the leading measurement spot are separately imaged by a common imaging collection objective onto one or more detectors. The imaging based collection design spatially separates the image of the leading measurement spot from the image of the primary measurement spot at one or more wafer image planes.

In a further aspect, light collected by an imaging objective passes through collection beam splitter that splits off a small portion of a primary measurement signal and a laser power measurement signal from the signals directed to the primary imaging detector. The beam splitting element of the collection beam splitter minimizes the signal loss from the primary measurement channel, while providing enough light for detection of the leading measurement spot. In some embodiments, the beam splitting element includes an aperture with a reflectance that varies depending on location across the beam to enhance detection of the leading measurement spot.

In another further aspect, a haze filter is employed to suppress background signal due to wafer surface irregularities and improve the signal to noise ratio of the detected signals.

In another further aspect, an obscuration is located in the beam path near the wafer image plane in front of the laser power management detector to selectively block either the image of the leading measurement spot or the primary measurement spot.

In another aspect, light detected from the leading measurement spot is analyzed to determine a reduced power time interval when the optical power of the primary illumination beam and the leading illumination beam are reduced to avoid damage or further contamination of the wafer under inspection.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

The inventive concepts described herein are based on the observation that larger particles (e.g., particles greater than one micron in diameter) are more likely to be damaged by the incident laser beam than smaller particles. For example, larger particles have more surface area, and as such, tend to absorb significantly more power than smaller particles having less surface area. Larger particles also tend to scatter significantly more light than smaller particles, due to larger surface area and/or increased surface irregularities. For example, the relative amount of light scattered from a particle of radius, R, is proportional to the particle radius raised to the sixth power. The tendency of large particles to strongly scatter light is exploited to reduce thermal damage during surface inspection.

In one aspect, a surface inspection system implements illumination power control functionality that determines the presence of a large particle in the inspection path of a primary measurement spot using a leading measurement spot and generates a control signal to reduce the incident illumination power before a relatively high power portion of the illumination reaches the large particle. In this manner, thermal damage may be avoided. Both the primary measurement spot and the leading measurement spot are separately imaged by a common imaging collection objective onto one or more detectors.

By monitoring large particles and dynamically adjusting illumination power, large particle blow-up and surface damage are avoided while maintaining stringent particle sensitivity requirements. In some embodiments, illumination power is switched to a low level when approaching a large particle and switched back to a high power level after the large particle is passed. In some embodiment, illumination power is maintained at a lower level when scanning the wafer center, or when scanning in the vicinity of structural features such as a notch, scribe mark, or wafer holding structures that tend to generate large amounts of scattered light.

Figure 1:
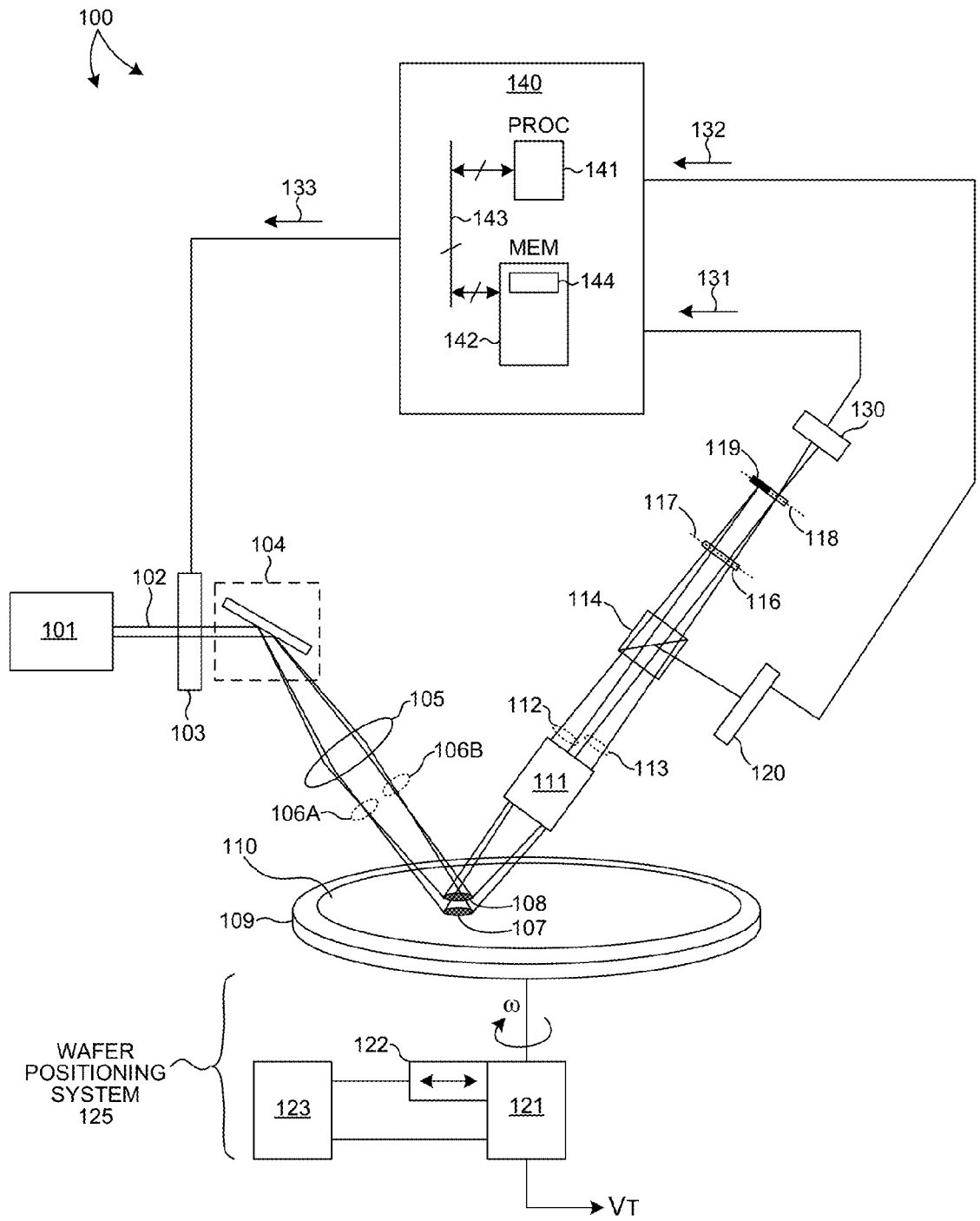
FIG. 1 is a simplified diagram illustrative of one embodiment of an inspection system configured to monitor large particle contamination and control the beam intensity of illumination light supplied to a specimen under inspection.

FIG. 1 is a simplified schematic view of one embodiment of a surface inspection system 100 that may be used to perform the inspection methods described herein. For simplification, some optical components of the system have been omitted. By way of example, folding mirrors, polarizers, beam forming optics, additional light sources, additional collectors, and additional detectors may also be included. All such variations are within the scope of the invention described herein. The inspection system described herein may be used for inspecting patterned, as well as unpatterned wafers.

As illustrated in FIG. 1, an illumination source 101 generates a beam of illumination light 102 that is directed toward wafer 110. As depicted in FIG. 1, illumination is provided to the surface of wafer 110 at an oblique angle by the illumination subsystem. However, in general, the illumination subsystem may be configured to direct the beam of light to the specimen at a normal angle of incidence. In some embodiments, system 100 may be configured to direct multiple beams of light to the specimen at different angles of incidence, such as an oblique angle and a normal angle of incidence. The multiple beams of light may be directed to the specimen substantially simultaneously or sequentially.

Illumination source 101 may include, by way of example, a laser, a diode laser, a helium neon laser, an argon laser, a solid state laser, a diode pumped solid state (DPSS) laser, a xenon arc lamp, a gas discharging lamp, and LED array, or an incandescent lamp. The light source may be configured to emit near monochromatic light or broadband light. In some embodiments, the illumination subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm) for an interval of time. Therefore, if the light source is a broadband light source, the illumination subsystem may also include one or more spectral filters that may limit the wavelength of the light directed to the specimen. The one or more spectral filters may be bandpass filters and/or edge filters and/or notch filters.

The beam of illumination light 102 is directed to illumination power control element 103. Illumination power control element 103 is configured to control the optical power of the beam of illumination light 102 in accordance with command signal 133 received from computing system 140. In one embodiment, illumination power control element 103 is located in the illumination beam path between illumination source 101 and beam splitting element 104 to dynamically adjust the illumination power during a surface inspection scan.

In a preferred embodiment, the illumination power control element 103 is a high efficiency, low cost, acousto-optic modulator (AOM). The optical power transmitted through the AOM is modulated by a radio frequency (RF) driver that provides fast switching capability without costly, high voltage drivers.

In general, illumination power control element 103 may be implemented with a selectively transmissive optical component, which may be adapted to transmit a portion of the incident light based on a polarization of the incident light. In some embodiments, illumination power control element 103 includes a wave plate (such as a quarter wave plate) and a polarizing beam splitter. In this configuration, the wave plate may be used to change the polarization of the incoming light, while the beam splitter functions to transmit one or more select polarizations (e.g., linearly polarized light) and reflect all others (e.g., randomly, circularly or elliptically polarized light). By reflecting portions of the light, the wave plate and beam splitter function to reduce the intensity or power level of the transmitted light. However, wave plates and similar optical components (e.g., neutral density filters) cannot be turned on and off like a switch, and instead, must be moved in and out of the beam path to provide two distinct power levels. In some cases, such movement may not be fast enough to provide dynamic power alteration during a surface inspection scan.

In some embodiments, illumination power control element 103 includes an electro-optical material that is switchable between an "on" condition and an "off" condition. When "on," the electro-optical material changes the polarization of the incoming light into a predetermined polarization orientation. This so-called "re-polarized light" may then be supplied to a polarizing beam splitter, which may transmit only a portion of the re-polarized light, depending on the particular polarization output from the electro-optical switch. Remaining portions of the re-polarized light may be reflected and discarded (e.g., absorbed by a beam dump material). In some cases, the electro-optical material may switch between "on" and "off" conditions within a time span of a few nanoseconds to a few microseconds.

In a specific embodiment, illumination power control element 103 includes a high-speed electrically-controlled optical shutter, known as a Pockel Cell. A Pockel Cell may be set in an "on" condition to allow the light generated by illumination source 101 to pass freely. When the presence of a large particle is detected, the Pockel Cell may be switched to an "off" condition to change the polarization of the generated light to a different polarization, which can be at least partially filtered out by a polarizing beam splitter. To switch between the "on" and "off" conditions, an electrical voltage provided by a variable power supply may be supplied to the Pockel Cell to change the polarization of the light passed through the electro-optical material (typically, an electro-optical crystal). The voltage supplied to the Pockel Cell may be determined by control signal 133 communicated from computing system 140.

In some embodiments, a constant power laser beam is generated by illumination source 101. Beam 102 is controlled at two distinct power levels (e.g., a "safe" power level and a "full" power level) by illumination power control element 103. The safe power level may be substantially less than the full power level to prevent thermal damage when scanning over large particles. For example, the safe power level may be some percentage (e.g., between about 1% and about 50%) of the full power level. In one embodiment, the safe power level may be about 1% of the full power level. Other possibilities exist and may generally depend on the incident laser power, as well as the size and material composition of the particles being scanned.

In some other embodiments, illumination power control element 103 is configured to generate more than two distinct power levels. For example, an AOM can be driven at any suitable frequency, and thus modulate illumination power over a broad range. In another example, a Pockel Cell can be driven to produce substantially any phase shift, and thus, may be combined with a polarizing beam splitter to create substantially any output power level. In some embodiments, circuitry and/or software may be included with illumination power control element 103 to provide a continuous power level adjustment (e.g., in the form of a closed feedback loop).

In general, the present invention may encompass any appropriate technique for dynamically altering the power level of an illumination source provided that the power control element provides a relatively fast response (e.g., on the order of a few nanoseconds to a few microseconds) and at least two distinct power levels (e.g., "safe" and "full" power levels).

After passing through illumination power control element 103, the illumination beam is directed to a beam splitting element 104 that generates a leading illumination beam 106A and a primary illumination beam 106B from illumination beam 102 generated by illumination source 101. The leading illumination beam 106A and the primary illumination beam 106B are directed to the wafer surface. The light that reaches the surface of the wafer may be altered in one or more ways, including polarization, intensity, size and shape, etc. In the embodiment depicted in FIG. 1, beam splitting element 104 directs leading illumination beam 106A and primary illumination beam 106B to an objective lens 105. Objective lens 105 focuses the leading illumination beam 106A and primary illumination beam 106B onto wafer 110 at leading measurement spot 107 and primary measurement spot 108, respectively.

In a preferred embodiment, beam splitting element 104 illuminates two spatially distinct, measurement spots 107 and 108. The illumination of leading measurement spot 107 is relatively low power, and the illumination of primary measurement spot 108 is relatively high power. In some examples, the overall illumination power of the leading measurement spot is less than ten percent of the overall illumination power of the primary measurement spot. The overall power of the leading measurement spot is selected just high enough to detect large particles, while the overall power of the primary measurement beam is maintained as high as possible to maximize defect sensitivity.

Figure 2:
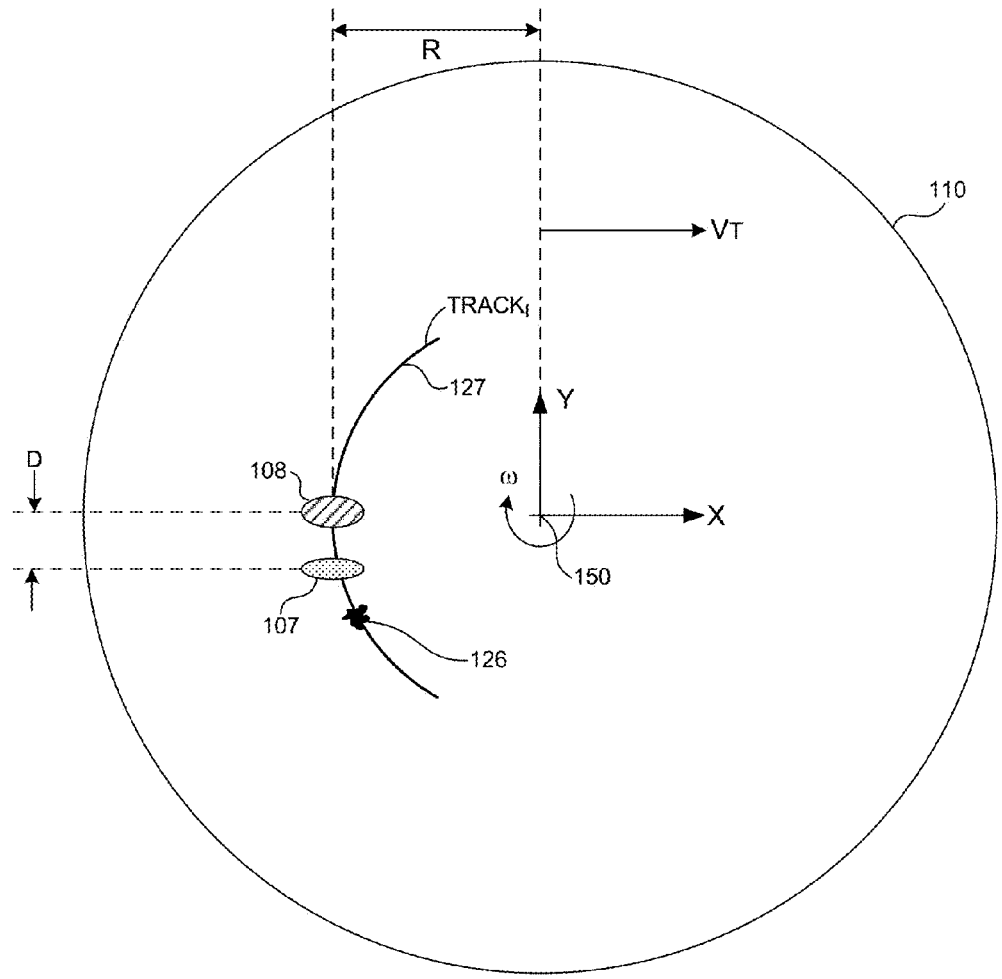
FIG. 2 is a simplified diagram illustrative of a wafer 110 illuminated by a leading illumination beam and primary illumination beam.

In the embodiment illustrated in FIG. 1, wafer positioning system 125 moves wafer 110 under leading illumination beam 106A and primary illumination beam 106B. Wafer positioning system 125 includes a wafer chuck 109, motion controller 123, a rotation stage 121 and a translation stage 122. Wafer 110 is supported on wafer chuck 109. As illustrated in FIG. 2, wafer 110 is located with its geometric center 150 approximately aligned the axis of rotation of rotation stage 121. In this manner, rotation stage 121 spins wafer 110 about its geometric center at a specified angular velocity, ω, within an acceptable tolerance. In addition, translation stage 122 translates the wafer 110 in a direction approximately perpendicular to the axis of rotation of rotation stage 121 at a specified velocity, $V_T$. Motion controller 123 coordinates the spinning of wafer 110 by rotation stage 121 and the translation of wafer 110 by translation stage 122 to achieve the desired scanning motion of wafer 110 within inspection system 100.

In an exemplary operational scenario, inspection begins with leading measurement spot 107 and primary measurement spot 108 located at the geometric center 150 of wafer 110 and then wafer 110 is rotated and translated until leading measurement spot 107 and primary measurement spot 108 reach the outer perimeter of wafer 110 (i.e., when R equals the radius of wafer 110). Due to the coordinated motion of rotation stage 121 and translation stage 122, the locus of points illuminated by leading measurement spot 107 and primary measurement spot 108 traces a spiral path on the surface of wafer 110. The spiral path on the surface of wafer 110 is referred to as an inspection track 127 (not shown in its entirety). A portion of an exemplary inspection track 127 is illustrated in FIG. 2 as TRACK$_i$.

As illustrated in FIG. 2, leading measurement spot 107 and primary measurement spot 108 are located a distance, R, from the geometric center of wafer 110. In a preferred embodiment, the leading measurement spot 107 is very similar in size and intensity profile as the primary measurement spot 108. In addition, the leading measurement spot 107 is located at a specific distance, D, ahead of the primary measurement spot 108 along the scan path at the wafer plane.

Figure 7:
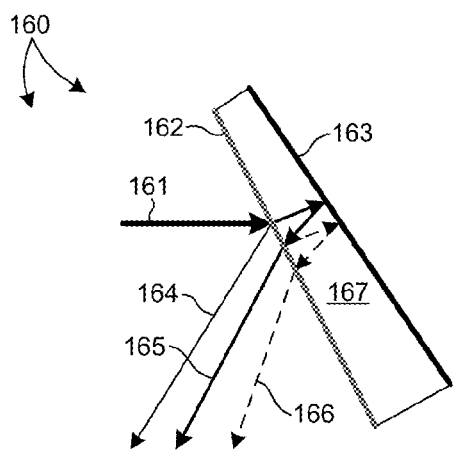
FIG. 7 depicts an embodiment of a wedge mirror beam splitter.

FIG. 7 depicts an embodiment 160 of a beam splitting element that, for example, may be implemented as beam splitting element 104 depicted in FIG. 1. Embodiment 160 is a wedge mirror beam splitter including a wedge shaped optical element 167. The incident surface 162 of the optical element 167 includes an optical coating that causes a small percentage of the incident beam 161 (e.g., less than ten percent) to reflect from the incident surface at the air-coating interface. The reflected light 164 forms the leading measurement beam. The remaining portion of incident beam 161 passes through the optical element 167 and is reflected from a backside surface 163 of optical element 167 that includes a mirror coating. At the incident surface 162, a large percentage of the beam is transmitted through the wedge-coating interface. The transmitted beam 165 forms the primary measurement beam that is spatially displaced from the leading measurement beam. A small portion of incident light remains trapped within the wedge optical element 167 and internally reflects again. A portion of this light passes through the wedge-coating interface and forms beam 166. This light is discarded (e.g., absorbed by another element of inspection system 100).

Figure 8:
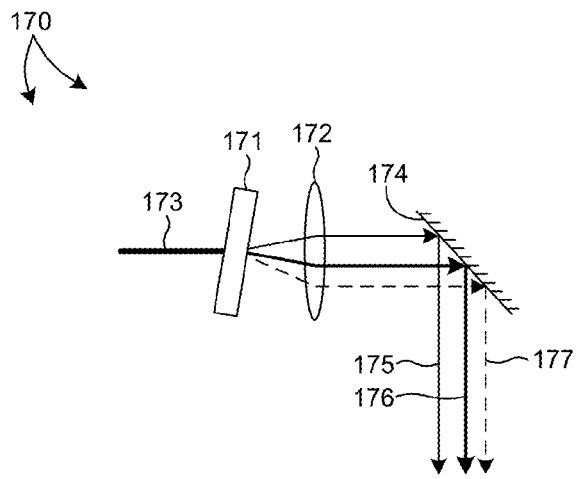
FIG. 8 depicts an embodiment of a beam splitter based on a diffractive optical element.

FIG. 8 depicts an embodiment 170 of a beam splitting element that, for example, may be implemented as beam splitting element 104 depicted in FIG. 1. Embodiment 170 is a diffractive optical element (DOE) based beam splitter including a DOE 171. Incident beam 173 is dispersed into different diffraction orders aligned with different directions by DOE 171. The dispersed light is approximately collimated by optics 172 and directed toward wafer 110 by mirror 174. In one example, −1 order diffracted light forms beam 175 that is employed as the leading measurement beam, +1 order diffracted light forms beam 176 that is employed as the primary measurement beam, and higher order diffracted light forms beam 177, which is discarded.

Figure 9:
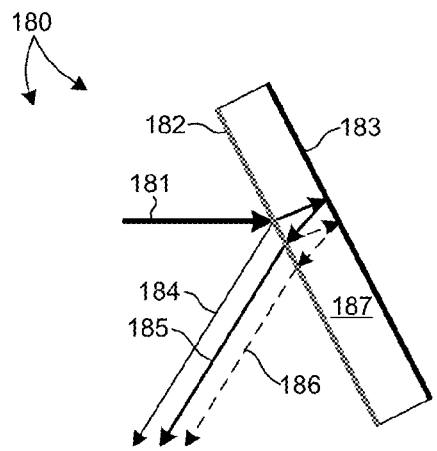
FIG. 9 depicts an embodiment of a beam splitter based on a parallel plate mirror beam splitter.

FIG. 9 depicts an embodiment 180 of a beam splitting element that, for example, may be implemented as beam splitting element 104 depicted in FIG. 1. Embodiment 180 is a parallel plate beam splitter including a rectangular shaped optical element 187. The incident surface 182 of the optical element 187 includes an optical coating that causes a small percentage of the incident beam 181 (e.g., less than ten percent) to reflect from the incident surface at the air-coating interface. The reflected light 184 forms the leading measurement beam. The remaining portion of incident beam 181 passes through the optical element 187 and is reflected from a backside surface 183 of optical element 187 that includes a mirror coating. At the incident surface 182, a large percentage of the beam is transmitted through the wedge-coating interface. The transmitted beam 185 forms the primary measurement beam that is spatially displaced from the leading measurement beam. A small portion of incident light remains trapped within the wedge optical element 187 and internally reflects again. A portion of this light passes through the wedge-coating interface and forms beam 186. This light is discarded (e.g., absorbed by another element of inspection system 100).

In one aspect, inspection system 100 includes an imaging collection objective 111 employed to image the light scattered and/or reflected from wafer 110 over a range of collection angles at both leading measurement spot 107 and primary measurement spot 108 onto one or more wafer image planes of the collection optics subsystem. The imaging based collection design spatially separates the image of the leading measurement spot from the image of the primary measurement spot at one or more wafer image planes. This allows the scattered signals associated with the primary measurement spot and the leading measurement spot to be independently detected even though the separation distance, D, between the primary measurement spot and the leading measurement spot is quite small (e.g., less than 250 micrometer). In one embodiment, the separation distance, D, is approximately 150 micrometers. The imaging based collection design also improves the dynamic range of the signal detection because the scattered light from the primary measurement spot is not mixed with the scattered light from the leading measurement spot.

Although a particular, nominal orientation of collection objective 111 is illustrated in FIG. 1, it is understood that the orientation of the collection objective with respect to the wafer surface may be arranged appropriately depending upon, for example, the angle of incidence and/or topographical characteristics of the wafer.

Figure 10:
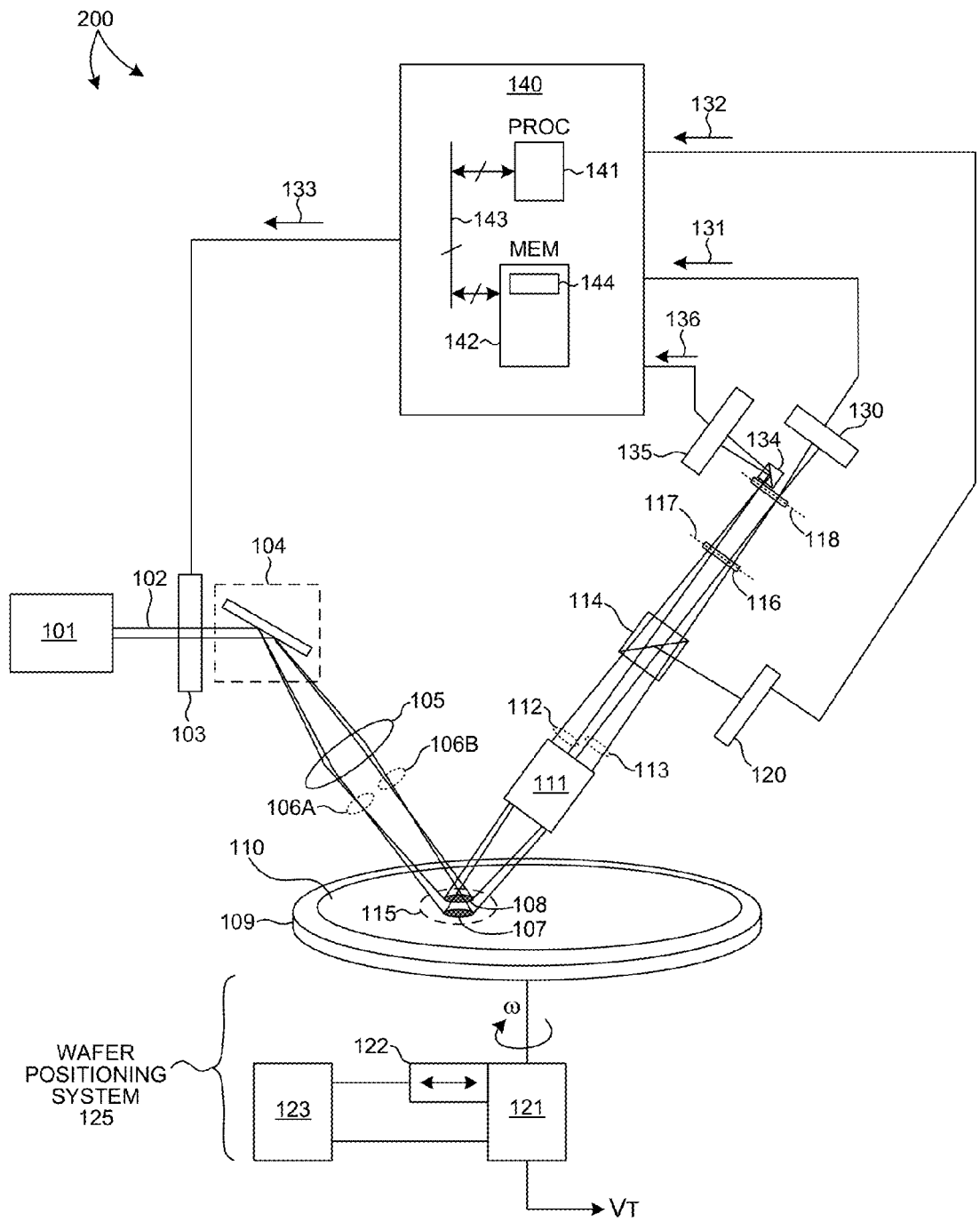
FIG. 10 is a simplified diagram illustrative of another embodiment of an inspection system configured to monitor large particle contamination and control the beam intensity of illumination light supplied to a specimen under inspection.
Figure 11:
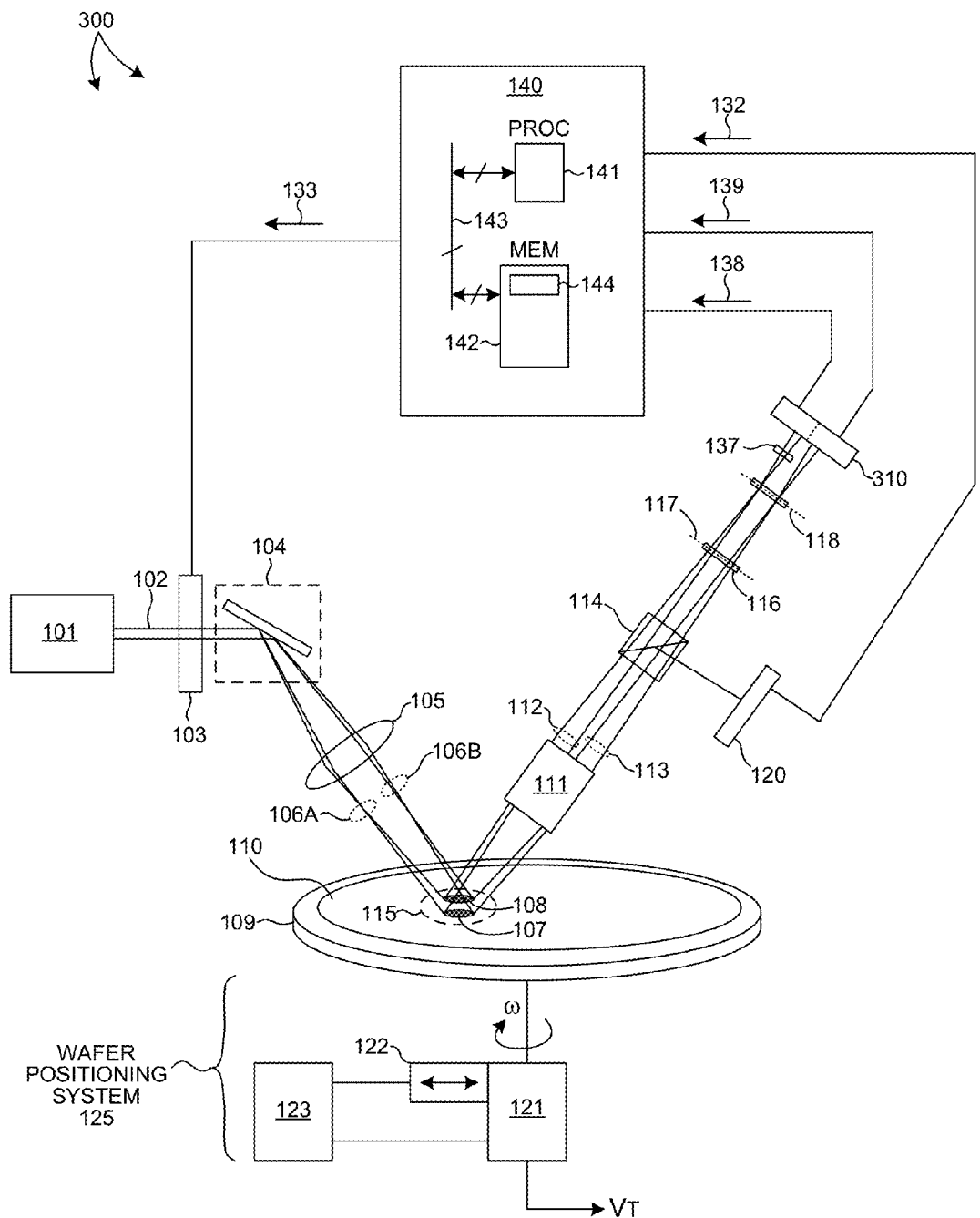
FIG. 11 is a simplified diagram illustrative of yet another embodiment of an inspection system configured to monitor large particle contamination and control the beam intensity of illumination light supplied to a specimen under inspection.

As depicted in FIG. 1, imaging objective 111 images light scattered and/or reflected from both leading measurement spot 107 and primary measurement spot 108. A portion 112 of the imaged light is associated with light scattered and/or reflected from the primary measurement spot 108 and a portion 113 of the imaged light is associated with light scattered and/or reflected from leading measurement spot 107. As depicted in FIGS. 1, 10, and 11, the collection optics are designed such that the laser power measurement channel shares most of the optical elements of the primary measurement channel.

In one aspect, light collected by imaging objective 111 passes through collection beam splitter 114 that splits off a small portion of the primary measurement signal and the laser power measurement signal from the signals directed to the primary imaging detector. The beam splitting element of the collection beam splitter 114 is designed to minimize the signal loss from the primary measurement channel, while providing enough light for leading beam detection. In this manner, the primary defect channels have sufficient signal to noise ratio to meet the defect detection requirements at the desired wafer throughput.

As depicted in FIG. 1, a relatively large proportion of the imaged light is directed to imaging detector 120. In some examples, more than 90% of the imaged light collected by imaging objective 111 is directed to imaging detector 120. In some examples, more than 95% of the imaged light collected by imaging objective 111 is directed to imaging detector 120. In some examples, more than 99% of the imaged light collected by imaging objective 111 is directed to imaging detector 120.

In some embodiments, the beam splitting element of collection beam splitter 114 includes a coating that reflects a relatively large percentage of incident light toward imaging detector 120 and transmits a relatively small percentage of incident light toward laser power management (LPM) detector 130. In some embodiments, the coating is uniformly applied on the beam splitting element, so that the proportion of light reflected is spatially uniform across the beam splitting element.

Figures 5A, 5B:
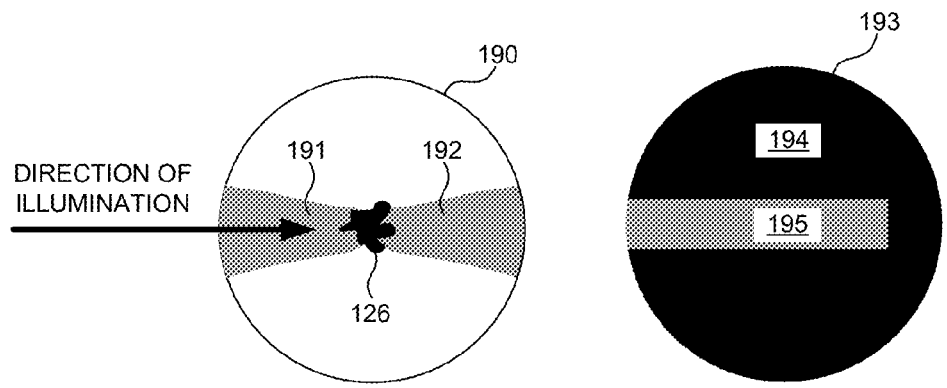
FIG. 5A depicts an image of a wafer within a field of view of an imaging objective.
FIG. 5B depicts an aperture including a highly reflective region that reflects practically all light incident to a collection beam splitter 114 within one region and another partially reflective region that transmits some light incident to the collection beam splitter within another region.

However, in a further aspect, the beam splitting element includes an aperture (e.g., a coating aperture) such that the proportion of light reflected varies depending on location across the beam splitting element. FIG. 5A depicts an image of the wafer 190 within the field of view of imaging objective 111. As illustrated in FIG. 5A, a large particle 126 is located within the field of view. The inventors have discovered that a significant portion of light scattered from large particles is scattered along the direction of illumination. FIG. 5A depicts forward scattered light 192 (i.e., projected in the direction of illumination). In addition, a significant portion of light scattered from large particle 126 is backward scattered light 191 (i.e., projected in the direction opposite the direction of illumination). To enhance the detection sensitivity of the leading measurement spot to the presence of large particles, an aperture is introduced to the collection beam splitter 114 that permits a higher transmission percentage toward the LPM detector 130 in the regions of forward and backscattered light than for other regions within the field of view. In one example, depicted in FIG. 5B, aperture 193 includes a highly reflective region 194 that reflects practically all light incident to collection beam splitter 114 within region 194 toward imaging detector 120. In addition, aperture 193 includes a reflective region 195 that is less reflective than highly reflective region 194. Light incident to collection beam splitter 114 within region 195 is partially reflected toward imaging detector 120 and partially transmitted toward LPM detector 130. In some embodiments, less than two percent of light incident to collection beam splitter 114 within region 195 is partially transmitted toward LPM detector 130.

Imaging detector 120 generally functions to convert the detected light into electrical signals 132 indicative of the detected image of the wafer 110 within the detected field of view. In general, imaging detector 120 may include substantially any photodetector known in the art. However, a particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may employed to increase the signal-to-noise ratio and throughput of the system. However, other detectors such as charge-coupled device (CCD) cameras, arrays of photodiodes, phototubes and photomultiplier tubes (PMTS) may be used, depending on the amount of light available for inspection and the type of inspection being performed.

Imaging detector 120 may be implemented in various imaging modes, such as bright field, dark field, and confocal. Various imaging modes such as bright field, dark field, and phase contrast can be implemented by using different apertures or Fourier filters. U.S. Pat. Nos. 7,295,303 and 7,130,039, which are incorporated by reference herein, describe these imaging modes in further detail. In another example (not shown), a detector generates dark field images by imaging scattered light collected at larger field angles. In another example, a pinhole that matches the incident spot 115 can be placed in front of a detector (e.g., detector 120) to generate a confocal image. U.S. Pat. No. 6,208,411, which is incorporated by reference herein, describes these imaging modes in further detail. In addition, various aspects of surface inspection system 100 are described in U.S. Pat. Nos. 6,271,916 and 6,201,601, both of which are incorporated herein by reference.

Figure 6:
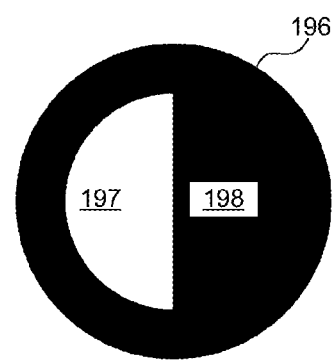
FIG. 6 depicts an aperture 196 that includes a highly reflective region 198 that blocks practically all forward scattered light depicted in FIG. 5A and transmits most back scattered light depicted in FIG. 5A.

In a further aspect, the portion of light transmitted through collection beam splitter 114 passes through a haze filter 116 approximately located at the pupil plane of the collection optics system. The surface of wafer 110 is not perfectly flat and polished. As a result, a background signal will be detected by the LPM detector 130. Haze filter 116 suppresses this background signal, thus improving the signal to noise ratio of the detected signals. The inventors have discovered that wafer haze is not spatially uniform, and in fact is strongly dependent on forward scattered light. To enhance the detection sensitivity of the leading measurement spot to the presence of large particles, an aperture is introduced at the pupil plane 117 as a haze filter. The aperture is configured to block a significant portion of forward scattered light. In one example, depicted in FIG. 6, aperture 196 includes a highly reflective region 198 that blocks practically all forward scattered light depicted in FIG. 5A and transmits most back scattered light depicted in FIG. 5A through region 197.

In another further aspect, an obscuration (e.g., edge mask) is located in the beam path near the wafer image plane in front of the LPM detector to selectively block either the image of the leading measurement spot or the primary measurement spot. This may be employed for calibration purposes, beam selection, or other configurations. In some examples, beam blocking mask at the wafer image plane improves the dynamic range of the detector.

As depicted in FIG. 1, inspection system 100 includes an obscuration 119 in the beam path of the portion 112 of the imaged light associated with light scattered and/or reflected from primary measurement spot 108 at or near the wafer image plane 118. In this manner, only scattered light originating from the leading measurement spot 107 is projected onto LPM detector 130.

An LPM detector generally functions to convert the detected light into electrical signals indicative of the amount of light scattered from the primary measurement spot, leading measurement spot, or both. In some embodiments, an LPM detector is an imaging detector. However, in some other embodiments, an LPM detector is a non-imaging detector configured to generate a single output signal indicative of the amount of light scattered from the primary measurement spot, leading measurement spot, or both. A single output signal allows for efficient detection of large particles with high throughput.

In general, an LPM detector may include substantially any photodetector known in the art. However, a particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may employed to increase the signal-to-noise ratio and throughput of the system. However, other detectors such as charge-coupled device (CCD) cameras, arrays of photodiodes, phototubes and photomultiplier tubes (PMTS) may be used, depending on the amount of light available for inspection and the type of inspection being performed.

In at least one embodiment of the invention depicted in FIG. 1, a single detector (e.g., an individual photomultiplier tube (PMT)) is employed as LPM detector 130 to detect light scattered from the leading measurement spot only. The output signal 131 of LPM detector 130 is communicated to a computing system 140 for processing to determine the presence of a large particle.

FIG. 10 depicts an inspection system in another embodiment 200. Inspection system 200 shares like numbered elements with inspection system 100. In the embodiment depicted in FIG. 10, two different detectors are employed to separately detect light scattered from the leading measurement spot and the primary measurement spot to obtain signal information at different power levels. As depicted in FIG. 10, LPM detector 130 detects light scattered from the leading measurement spot only and communicates signal 131 indicative of the detected light to computing system 140. In addition, inspection system 200 includes LPM detector 135 (e.g., a single PMT) configured to detect light scattered from the primary measurement spot only. Corner cube 134 directs a portion of the light imaged from the primary measurement spot 108 toward detector 135. The output signal 136 of LPM detector 135 is communicated to computing system 140 for processing to determine the presence of a large particle.

FIG. 11 depicts an inspection system in another embodiment 300. Inspection system 300 shares like numbered elements with inspection system 100. In the embodiment depicted in FIG. 11, an array detector 310 is employed to separately detect light scattered from the leading measurement spot and the primary measurement spot to obtain signal information. As depicted in FIG. 11, LPM detector 310 detects light scattered from the leading measurement spot and communicates signal 139 indicative of the detected light to computing system 140. In addition, LPM detector 310 detects light scattered from the primary measurement spot and communicates signal 138 indicative of the detected light to computing system 140. An attenuation element 137 is located in the optical path of the light imaged from the primary measurement spot to avoid saturation at array detector 310. In some embodiments, an array of detecting elements (e.g., a 32 pixel linear PMT array) is employed in an imaging mode to increase detector resolution and image both the leading measurement spot and the primary measurement spot incident on array detector 310.

Figure 12:
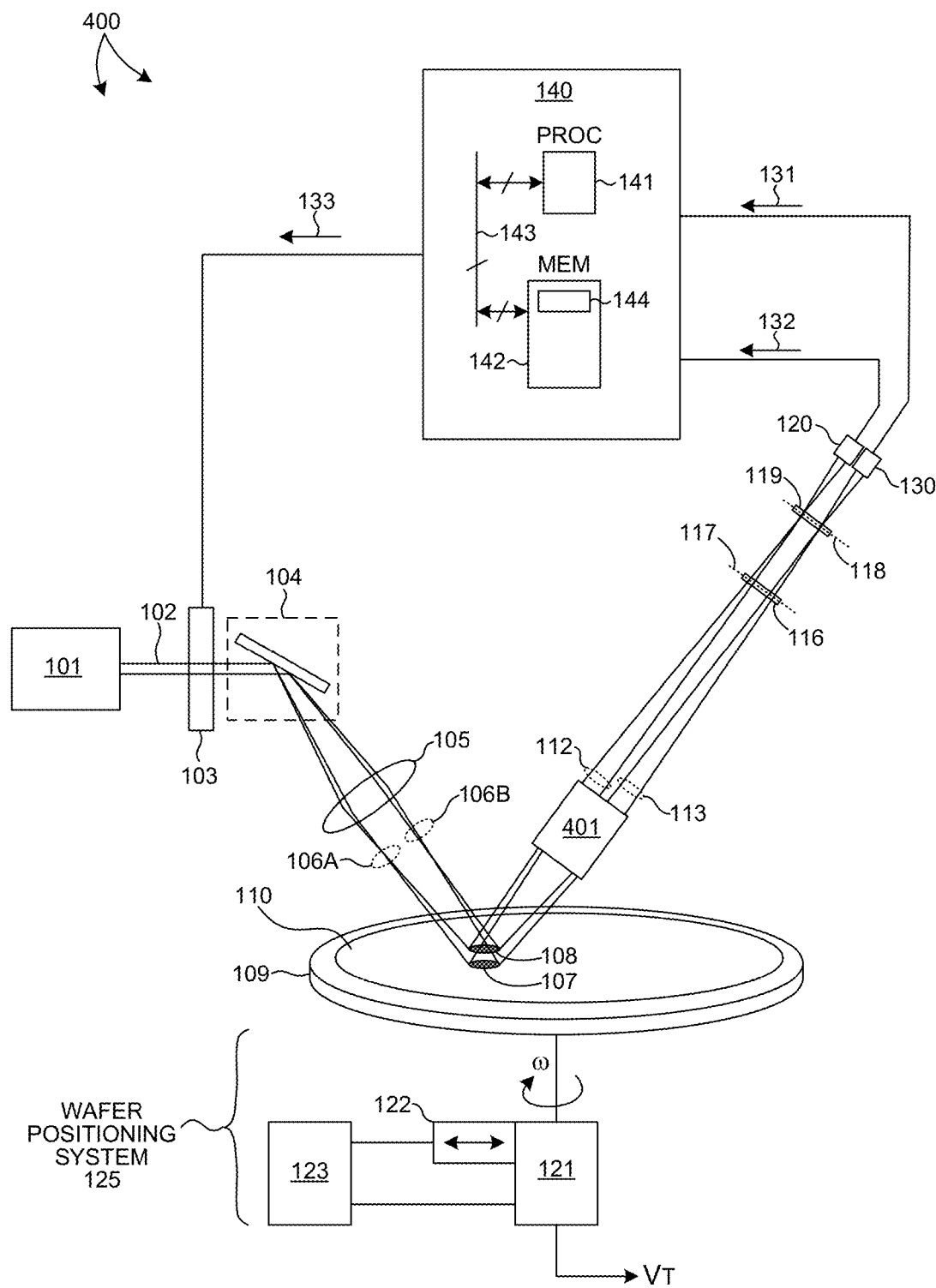
FIG. 12 is a simplified diagram illustrative of yet another embodiment of an inspection system configured to monitor large particle contamination and control the beam intensity of illumination light supplied to a specimen under inspection.

FIG. 12 depicts an inspection system in another embodiment 400. Inspection system 400 shares like numbered elements with inspection system 100. In the embodiment depicted in FIG. 12, collection imaging objective 401 is configured to image light scattered from the leading measurement spot and image light scattered from the primary measurement spot at spatially separated locations at image plane 118 without the use of a collection beam splitter. In this manner, all of the imaged light associated with light scattered and/or reflected from the primary measurement spot 108 and all of the imaged light associated with light scattered and/or reflected from leading measurement spot 107 are available for detection at separate locations. In the embodiment depicted in FIG. 12 imaging detector 120 is located near wafer image plane 118 and in the beam path of the imaged light associated with light scattered and/or reflected from the primary measurement spot 108. Similarly, LPM detector 130 is located near wafer image plane 118 and in the beam path of the imaged light associated with light scattered and/or reflected from the leading measurement spot 107. In general, additional optical elements (not shown) may be included to direct the spatially separated beams at image plane 118 toward the respective detectors.

In a further aspect, computing system 140 is configured to determine the size of a large particle in the scan path based on changes in the detected signals detected from the leading measurement spot. Based on the particle size, the illumination power is reduced to a level that avoids particle explosion, and the consequent proliferation of contaminants on the wafer surface.

As depicted in FIG. 2, large particle 126 is on the scan path approaching the leading measurement spot 107. Large particle 126 will first pass through the leading measurement spot 107, and a short time later, it will pass under primary measurement spot 108. As illustrated in FIG. 2, the leading measurement spot 107 is separated from the primary measurement spot 108 by a separation distance, D. In this example, the separation distance, D, is approximately 150 micrometers. In the time that it takes for the large particle 126 to travel the distance, D, inspection system 100 must sense the presence of large particle 126, estimate its size, and reduce the illumination power for the time that large particle 126 is within the field of view of primary measurement spot 108.

Figure 3:
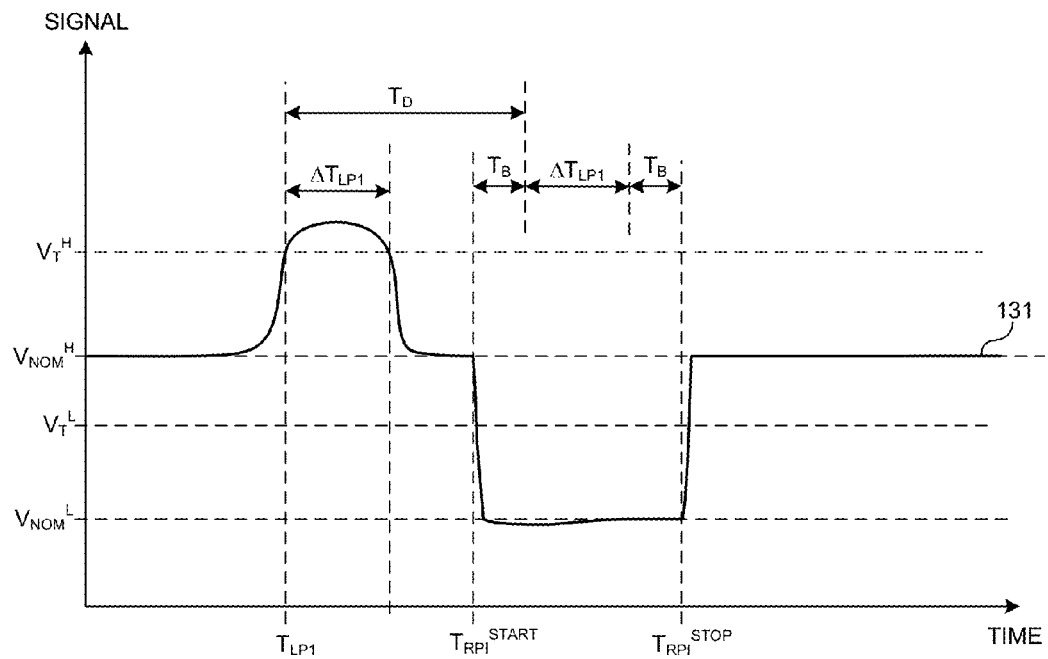
FIG. 3 is an illustration of a time plot of a signal communicated from a large particle detector of an inspection system in one operational scenario.

FIG. 3 depicts an illustration of a time plot of signal 131 communicated from detector 130 to computing system 140 in one operational scenario. Computing system 140 receives consecutive instances of signal 131 from detector 130 indicating the amount of scattered light received from the leading measurement spot 107 at each measurement time. Computing system 140 compares the amplitude of this signal with a predetermined threshold value, $V_T^H$, to determine if the amount of scattered light exceeds the threshold value. Referring to FIG. 3, computing system 140 determines that signal 131 exceeds a predetermined threshold value, $V_T^H$, at time, $T_{LP1}$, and remains above $V_T^H$ for a period of time, $\Delta T_{LP1}$. At this point, computing system 140 estimates when illumination power should be reduced and when the illumination power should be subsequently restored to avoid dosing the large particle with high energy illumination. In one example, computing system estimates a delay time, $T_D$, between the leading measurement spot 107 and the primary measurement spot 108 by dividing the known separation distance, D, by the known velocity of the wafer surface under inspection (e.g., $V_s = \omega * R + V_T$). The minimum length of time that the illumination power should be reduced is the period of time, $\Delta T_{LP1}$, when the large particle was sensed at the leading measurement spot (assuming that the size of the leading measurement spot is approximately the same as the primary measurement spot). In addition, computing system 140 adds a buffer time, $T_B$, on both ends of the time period, $\Delta T_{LP1}$, to arrive a reduced power interval having a duration of $\Delta T_{LP1} + 2*T_B$. Computing system 140 communicates a command signal 133 to illumination power control element 103 to initiate a reduced power interval at a time, $T_{RPI}^{START}$. $T_{RPI}^{START}$ is advanced in time by an amount $T_D - T_B$ from $T_{LP1}$. Similarly, computing system 140 communicates a command signal 133 to illumination power control element 103 to terminate the reduced power interval at a time $T_{RPI}^{STOP}$. The buffer time is added to the reduced power interval to accommodate any errors in the estimation of the size of the particle and its location (e.g., due to quantization effects, etc.). As illustrated in FIG. 3, signal 131, indicative of an amount of light detected from leading measurement spot 107, is muted during the reduced power interval, when the illumination power is reduced.

Figure 4:
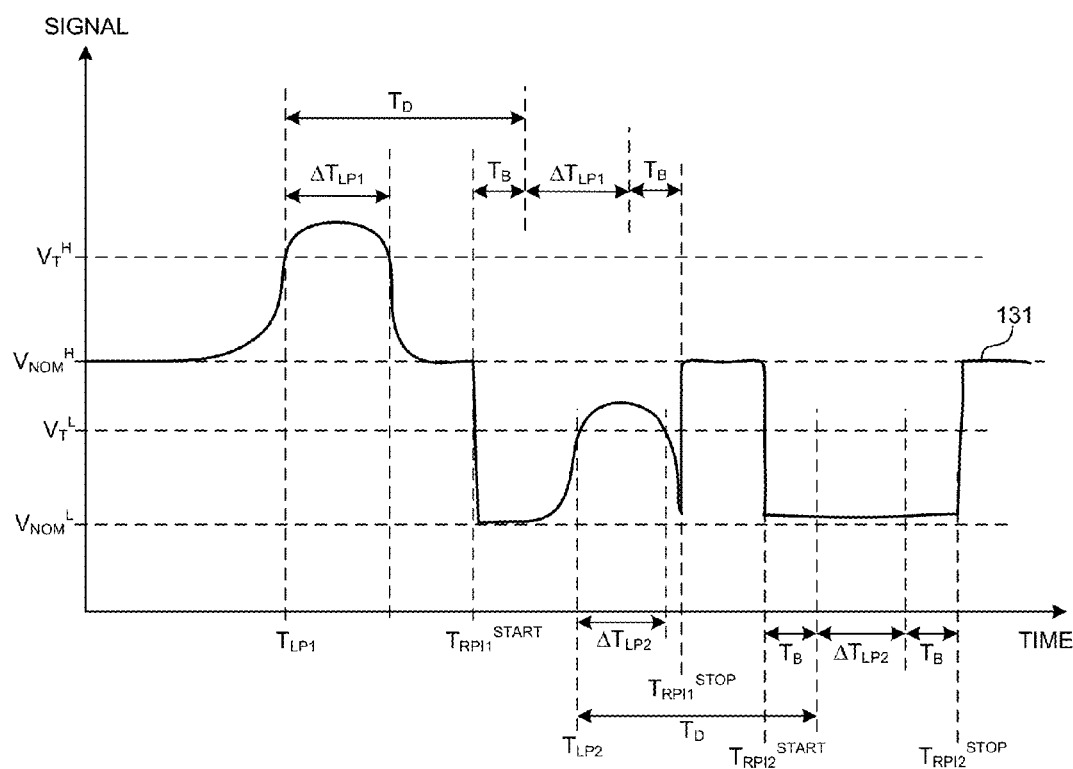
FIG. 4 is an illustration of a time plot of a signal communicated from a large particle detector of an inspection system in another operational scenario.

FIG. 4 depicts an illustration of a time plot of signal 131 communicated from detector 130 to computing system 140 in another operational scenario. In this operational scenario, two large particles are detected consecutively. Referring to FIG. 4, computing system 140 determines that signal 131 exceeds a predetermined threshold value, $V_T^H$, at time, $T_{LP1}$, and remains above $V_T^H$ for a period of time, $\Delta T_{LP1}$. At this point, computing system 140 estimates when illumination power should be reduced and when the illumination power should be subsequently restored to avoid dosing the first large particle with high energy illumination. As described with reference to FIG. 3, computing system estimates a delay time, $T_D$, between the leading measurement spot 107 and the primary measurement spot 108 and determines a reduced power interval having a duration of $\Delta T_{LP1}+2*T_B$. Computing system 140 communicates a command signal 133 to illumination power control element 103 to initiate a reduced power interval at a time, $T_{RPl1}^{START}$ and to terminate the reduced power interval at a time $T_{RPl1}^{STOP}$. $T_{RPl1}^{START}$ is advanced in time by an amount $T_D-T_B$ from $T_{LP1}$. During the reduced power interval, signal 131 is muted. However, there is sufficient signal level to continue monitoring for subsequent large particles. This is achieved by introducing a reduced, predetermined threshold value, $V_T^L$, during the reduced power interval. As depicted in FIG. 4, computing system 140 determines that signal 131 exceeds the reduced, predetermined threshold value, $V_T^L$, at time, $T_{LP2}$, and remains above $V_T^L$ for a period of time, $\Delta T_{LP2}$. At this point, computing system 140 estimates when illumination power should be reduced and when the illumination power should be subsequently restored to avoid dosing the second large particle with high energy illumination. Computing system estimates a delay time, $T_D$, between the leading measurement spot 107 and the primary measurement spot 108 and determines a reduced power interval having a duration of $\Delta T_{LP2}+2*T_B$. Computing system 140 communicates a command signal 133 to illumination power control element 103 to initiate a reduced power interval at a time, $T_{RPl2}^{START}$ and to terminate the reduced power interval at a time $T_{RPl2}^{STOP}$. $T_{RPl2}^{START}$ is advanced in time by an amount $T_D-T_B$ from $T_{LP2}$. After the termination of the second reduced power interval, the illumination power is returned to the normal level, along with the use of predetermined threshold value, $V_T^H$.

Inspection systems 100, 200, 300, and 400 also include various electronic components (not shown) needed for processing the scattered signals detected by the detectors. For example, systems 100, 200, 300, and 400 may include amplifier circuitry to receive signals from the detectors and to amplify the signals by a predetermined amount. In some embodiments, an analog-to-digital converter (ADC) (not shown) is included to convert the amplified signals into a digital format suitable for use within computing system 140. In one embodiment, the processor 141 may be coupled directly to an ADC by a transmission medium. Alternatively, the processor 141 may receive signals from other electronic components coupled to the ADC. In this manner, the processor may be indirectly coupled to the ADC by a transmission medium and any intervening electronic components.

In general, computing system 140 is configured to detect features, defects, or light scattering properties of the wafer using electrical signals obtained from each detector. The computing system 140 may include any appropriate processor(s) known in the art. In addition, the computing system 140 may be configured to use any appropriate defect detection algorithm or method known in the art. For example, the computing system 140 may use a die-to-database comparison or a thresholding algorithm to detect defects on the specimen.

In addition, inspection systems 100, 200, 300, and 400 may include peripheral devices useful to accept inputs from an operator (e.g., keyboard, mouse, touchscreen, etc.) and display outputs to the operator (e.g., display monitor). Input commands from an operator may be used by computing system 140 to adjust threshold values used to control illumination power. The resulting power levels may be graphically presented to an operator on a display monitor.

Inspection systems 100, 200, 300, and 400 include a processor 141 and an amount of computer readable memory 142. Processor 141 and memory 142 may communicate over bus 143. Memory 142 includes an amount of memory 144 that stores a program code that, when executed by processor 141, causes processor 141 to execute the power control and defect detection functionality described herein.

Although, illumination power control has been described hereinbefore with reference to a leading measurement spot and a primary measurement spot, the methods and systems described herein may also be applied analogously to a multi-spot surface inspection system. In a multi-spot inspection system, a number of leading and primary illumination spots are employed simultaneously. Illumination light is supplied to these illumination spots from one or more illumination sources. Typically, sets of leading measurement spots and primary measurement spots are configured with considerable spacing between sets of spots such that inspection results may be interleaved among successive portions of an inspection track and cross-talk at the detectors is minimized. U.S. Pat. Publication No. 2009/0225399, which is incorporated by reference herein, describes multi-spot scanning techniques in further detail.

Figure 13:
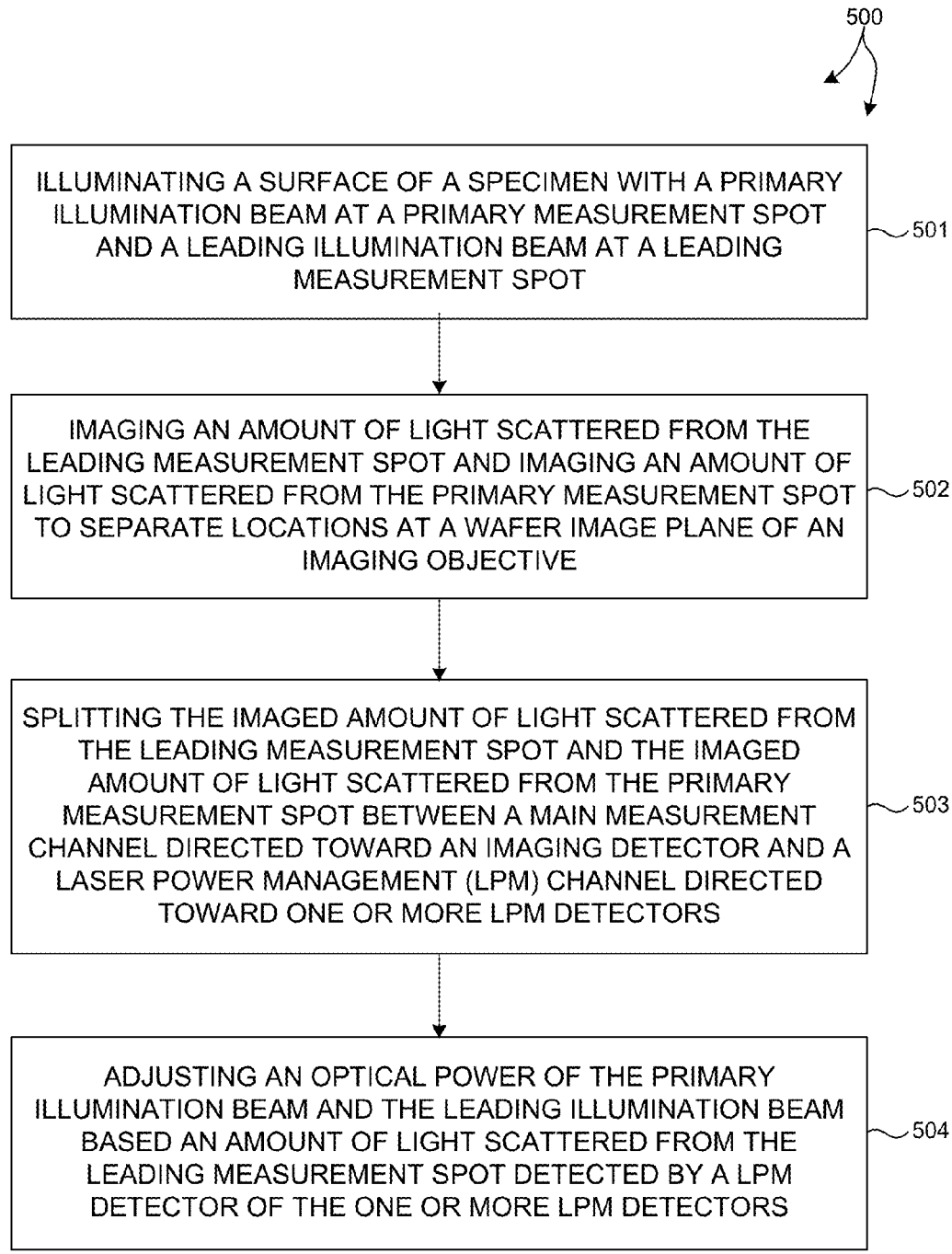
FIG. 13 illustrates a flowchart of an exemplary method 500 useful for monitoring large particles and controlling illumination power to improve defect sensitivity without inducing thermal damage on a wafer surface.

FIG. 13 illustrates a flowchart of an exemplary method 500 useful for monitoring large particles and controlling illumination power to improve defect sensitivity without inducing thermal damage to a wafer surface. In some non-limiting examples, inspection systems 100, 200, 300, and 400 described with reference to FIG. 1, FIG. 10, and FIG. 11, respectively, are configured to implement method 500. However, in general, the implementation of method 500 is not limited by the specific embodiments described herein.

In block 501, a surface of a specimen is illuminated with a primary illumination beam at a primary measurement spot and a leading illumination beam at a leading measurement spot.

In block 502, an amount of light scattered from the leading measurement spot and an amount of light scattered from the primary measurement spot are imaged to separate locations at a wafer image plane of an imaging objective.

In block 503, the imaged amount of light scattered from the leading measurement spot and the imaged amount of light scattered from the primary measurement spot are split between a main measurement channel directed toward an imaging detector and a laser power management (LPM) channel directed toward one or more LPM detectors.

In block 504, an optical power of the primary illumination beam and the leading illumination beam is adjusted based an amount of light scattered from the leading measurement spot detected by a LPM detector of the one or more LPM detectors.

Various embodiments are described herein for an inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. In one example, detector 140 can be replaced by a fiber array. In one example, inspection system 100 may include more than one light source (not shown). The light sources may be configured differently or the same. For example, the light sources may be configured to generate light having different characteristics that can be directed to a wafer at the same or different illumination areas at the same or different angles of incidence at the same or different times. The light sources may be configured according to any of the embodiments described herein. In addition one of the light sources may be configured according to any of the embodiments described herein, and another light source may be any other light source known in the art. In some embodiments, an inspection system may illuminate the wafer over more than one illumination area simultaneously. The multiple illumination areas may spatially overlap. The multiple illumination areas may be spatially distinct. In some embodiments, an inspection system may illuminate the wafer over more than one illumination area at different times. The different illumination areas may temporally overlap (i.e., simultaneously illuminated over some period of time). The different illumination areas may be temporally distinct. In general, the number of illumination areas may be arbitrary, and each illumination area may be of equal or different size, orientation, and angle of incidence. In yet another example, inspection system 100 may be a scanning spot system with one or more illumination areas that scan independently from any motion of wafer 110. In some embodiments an illumination area is made to scan in a repeated pattern along a scan line. The scan line may or may not align with the scan motion of wafer 110. Although as presented herein, wafer positioning system 125 generates motion of wafer 110 by coordinated rotational and translational movements, in yet another example, wafer positioning system 125 may generate motion of wafer 110 by coordinating two translational movements. For example motion wafer positioning system 125 may generate motion along two orthogonal, linear axes (e.g., X-Y motion). In such embodiments, scan pitch may be defined as a distance between adjacent translational scans along either motion axis. In such embodiments, an inspection system includes an illumination source and a wafer positioning system. The illumination source supplies an amount of radiation to a surface of a wafer over an illumination area. The wafer positioning system moves the wafer in a scanning motion characterized by a scan pitch (e.g., scanning back and forth in one direction and stepping by an amount equal to the scan pitch in the orthogonal direction).

Accordingly, various modifications, adaptations, and combinations of various features of the described embodiments can be practiced without departing from the scope of the invention as set forth in the claims.

What is claimed is:

1. A surface inspection system comprising:
an illumination source configured to generate a beam of illumination light;
a beam splitting element configured to split the beam of illumination light into a leading illumination beam and a primary illumination beam;
an illumination objective configured to project the leading illumination beam and the primary illumination beam onto a surface of a wafer at a leading measurement spot and a primary measurement spot, respectively;
an imaging objective configured to image an amount of light scattered from the leading measurement spot and image an amount of light scattered from the primary measurement spot to separate locations at a wafer image plane of the imaging objective;
a collection beam splitter configured to split the imaged amount of light scattered from the leading measurement spot and the imaged amount of light scattered from the primary measurement spot between a main measurement channel directed toward an imaging detector and a laser power management (LPM) channel directed toward one or more LPM detectors, wherein the collection beam splitter includes an aperture that subdivides a field of view of the collection beam splitter into at least one region aligned with a direction of illumination, wherein the aperture directs a higher percentage of light in the at least one region toward the one or more LPM detectors than any other region within the field of view, the one or more LPM detectors configured to generate an output signal indicative of the amount of light scattered from the leading measurement spot; and a computing system configured to:
receive the output signal indicative of the amount of light scattered from the leading measurement spot; and communicate a command signal to an illumination power control element that causes the illumination power control element to adjust an optical power of the beam of illumination light based on the output signal.

2. The surface inspection system of claim 1, further comprising:
a wafer positioning system operable to move the wafer in a scanning motion such that the leading measurement spot and the primary measurement spot move across the surface of the wafer along an inspection path.

3. The surface inspection system of claim 2, wherein the leading measurement spot is located ahead of the primary measurement spot in the inspection path and is separated from the primary measurement spot by a predetermined separation distance.

4. The surface inspection system of claim 1, wherein the output signal indicative of the amount of light scattered from the leading measurement spot is a single valued signal.

5. The surface inspection system of claim 1, wherein the output signal indicative of the amount of light scattered from the leading measurement spot is indicative of an image of the light scattered from the leading measurement spot.

6. The surface inspection system of claim 1, wherein the illumination power control element is an acousto-optic modulator.

7. The surface inspection system of claim 1, further comprising:
a haze filter located in an optical path between the imaging objective and the one or more LPM detectors at or near a pupil plane of the imaging objective.

8. The surface inspection system of claim 1, wherein the collection beam splitter includes an aperture that directs a larger proportion of backscattered light and forward scattered light into the LPM channel than other light scattered from the leading measurement spot.

9. The surface inspection system of claim 1, further comprising:
an obscuration element located in an optical path of the LPM channel, the obscuration element configured to selectively block the imaged amount of light scattered from the primary measurement spot or the imaged amount of light scattered from the leading measurement spot in the LPM channel at or near a wafer image plane in front of an LPM detector of the one or more LPM detectors.

10. The surface inspection system of claim 1, wherein a first LPM detector of the one or more LPM detectors generates an output signal indicative of the amount of light scattered from the leading measurement spot and a second LPM detector of the one or more LPM detectors generates an output signal indicative of the amount of light scattered from the primary measurement spot.

11. The surface inspection system of claim 1, wherein an array detector of the one or more LPM detectors generates a first output signal indicative of the amount of light scattered from the leading measurement spot and a second output signal indicative of the amount of light scattered from the primary measurement spot.

12. The surface inspection system of claim 1, wherein the command signal to the illumination power control element causes the illumination power control element to reduce the optical power of the beam of illumination light for a reduced power time interval after the output signal indicative of the amount of light scattered from the leading measurement spot exceeds a predetermined threshold value.

13. The surface inspection system of claim 12, wherein the reduced power time interval includes an amount of time the leading measurement spot exceeds the predetermined threshold value.

14. The surface inspection system of claim 12, wherein the reduced power time interval is initiated at a fixed time after the output signal indicative of the amount of light scattered from the leading measurement spot exceeds a predetermined threshold value, wherein the fixed time is a function of a separation distance between the leading measurement spot and the primary measurement spot.

15. A method comprising:
illuminating a surface of a specimen with a primary illumination beam at a primary measurement spot and a leading illumination beam at a leading measurement spot;

imaging an amount of light scattered from the leading measurement spot and imaging an amount of light scattered from the primary measurement spot to separate locations at a wafer image plane of an imaging objective;

splitting the imaged amount of light scattered from the leading measurement spot and the imaged amount of light scattered from the primary measurement spot between a main measurement channel directed toward an imaging detector and a laser power management (LPM) channel directed toward one or more LPM detectors, wherein the splitting involves subdividing a collection field of view into at least one region aligned with a direction of illumination, and directing a higher percentage of light in the at least one region toward the one or more LPM detectors than any other region within the field of view; and adjusting an optical power of the primary illumination beam and the leading illumination beam based an amount of light scattered from the leading measurement spot detected by a LPM detector of the one or more LPM detectors.

16. The method of claim 15, further comprising:
moving the specimen in a scanning motion such that the leading measurement spot and the primary measurement spot move across the surface of the speciment along an inspection path, wherein the leading measurement spot is located ahead of the primary measurement spot in the inspection path and is separated from the primary measurement spot by a predetermined separation distance.

17. The method of claim 15, further comprising:
selectively blocking the imaged amount of light scattered from the primary measurement spot or the imaged amount of light scattered from the leading measurement spot in the LPM channel at or near a wafer image plane in front of an LPM detector of the one or more LPM detectors.

18. The method of claim 15, wherein the optical power of the primary illumination beam and the optical power of the leading illumination beam are reduced for a reduced power time interval initiated after the output signal indicative of the amount of light scattered from the leading measurement spot exceeds a predetermined threshold value.

19. An apparatus comprising:
an illumination subsystem configured to project a leading illumination beam and a primary illumination beam onto a surface of a wafer at a leading measurement spot and a primary measurement spot, respectively;
an imaging objective configured to image an amount of light scattered from the leading measurement spot and image an amount of light scattered from the primary measurement spot to separate locations at a wafer image plane of the imaging objective;
a collection beam splitter configured to split the imaged amount of light scattered from the leading measurement spot and the imaged amount of light scattered from the primary measurement spot between a main measurement channel directed toward an imaging detector and a laser power management (LPM) channel directed toward one or more LPM detectors, wherein the collection beam splitter includes an aperture that subdivides a field of view of the collection beam splitter into at least one region aligned with a direction of illumination, wherein the aperture directs a higher percentage of light in the at least one region toward the one or more LPM detectors than any other region within the field of view, the one or more LPM detectors configured to generate an output signal indicative of the amount of light scattered from the leading measurement spot; and
a computing system comprising:
one or more processors; and
a non-transitory, computer-readable medium storing instructions that, when executed by the one or more processors, cause the apparatus to:
receive the output signal indicative of the amount of light scattered from the leading measurement spot; and
communicate a command signal to an illumination power control element that causes the illumination power control element to adjust an optical power of the beam of illumination light based on the output signal.

20. The apparatus of claim 19, wherein the optical power of the primary illumination beam and the optical power of the leading illumination beam are reduced for a reduced power time interval initiated after the output signal indicative of the amount of light scattered from the leading measurement spot exceeds a predetermined threshold value.

\* \* \* \* \*